United States Patent [19]

Ishikawa

[11] Patent Number: 6,090,823
[45] Date of Patent: Jul. 18, 2000

[54] REMEDY FOR SPINAL INJURY

[75] Inventor: Toshizo Ishikawa, Yamaguchi-ken, Japan

[73] Assignee: Chugai Seiyaku Kabushiki Kaisha, Tokyo, Japan

[21] Appl. No.: 09/155,182

[22] PCT Filed: Mar. 24, 1997

[86] PCT No.: PCT/JP97/00954

§ 371 Date: Jan. 21, 1999

§ 102(e) Date: Jan. 21, 1999

[87] PCT Pub. No.: WO97/35577

PCT Pub. Date: Oct. 2, 1997

[30] Foreign Application Priority Data

Mar. 22, 1996 [JP] Japan ................................ 8-065998

[51] Int. Cl.$^7$ .................................................. A61K 31/445
[52] U.S. Cl. ............................ 514/315; 514/343; 514/766
[58] Field of Search ...................................... 514/315, 824, 514/343, 766; 546/262

[56] References Cited

U.S. PATENT DOCUMENTS 4,366,161  12/1982  Mori et al. ............................. 514/332

*Primary Examiner*—Elli Peselev
*Attorney, Agent, or Firm*—Browdy and Neimark

[57] ABSTRACT (+)-N,N'-Propylene dinicotinamide or pharmaceutically acceptable salts thereof are outstanding drugs of high safety that can heal or ameliorate spinal cord injuries, prevent the transition from an incomplete cord injury to a complete injury, and minimize the consequences of spinal cord injuries including neurological disorders such as quadriplegia, paralysis of the respiratory muscle, damage to sensory functions and impairment of reflex functions, as well as impaired urinating or defecating functions.

9 Claims, 2 Drawing Sheets

LIII-IV

LI-II

REMEDY FOR SPINAL INJURY

TECHNICAL FIELD

This invention relates to a therapeutic agent for spinal cord injuries that is characterized by containing (+)-N,N'-propylene dinicotinamide (commonly known as "nicaraven") or a pharmaceutically acceptable salt thereof as an active ingredient.

BACKGROUND ART

Spinal cord injuries are diseases that involve traumatic injuries, malpositions, fractures and so forth of the spine and that manifest lesions such as edema, minor hemorrhage and necrosis within the spinal cord to cause disorders in the movement of the four limbs, as well as in sensory functions, urinary elimination and so forth. The occurrence of spinal cord injuries is particularly frequent in the cervical segments and the thoracolumbar transition where the spinal cavity is narrow.

Most spinal cord injuries are traumatic and caused by traffic accidents, athletic accidents, falls and drops from heights, and so forth. They are known to occur, seldom though, as direct injury due to a puncturing needle, an injury to the femoral artery which results in a ischemic damage to regions it dominates, and as complications of high spinal anesthesia and peridural anesthesia that are caused by spinal cord compression and so forth due to the formation of hematoma in the peridural space.

Among the spinal cord injuries, those occurring in the upper cervical segments are often fatal since they cause quadriplegia and paralysis of the respiratory muscle; even if the patient survives, he is so seriously affected that he is paralyzed in all four limbs and must live his life under assisted respiration. The injury may be below the upper cervical segments but if it is a complete cord injury, flaccid paralysis of the four limbs below the level of the injury, a loss of sensory and reflex functions, as well as an extinction of urinating or defecating functions are occasionally immediate consequences. In an incomplete cord injury, the symptoms mentioned above may initially appear due to edema and a softening of the central part of the spinal cord but, the patient tends to recover from the injury in about 3–4 weeks, so it may well be described as less serious than the complete cord injury.

For the treatment of such spinal cord injuries, steroids have been known to be effective (see Spine, 19(20), 2281–2287, 1994; J. Spinal Disord., 5(1), 125–131, 1992; J. Neurosurg., 63(5), 703–713, 1985; JAMA, 251(1), 45–52, 1984, etc.) Among the steroids, dexamethasone and methylprednisolone administered in high doses are held to be effective in ameliorating the neurological symptoms of spinal cord injuries (J. Spinal Disord., 5(1), 125–131, 1992.).

Massive administration of steroids which is conventionally known to be effective against spinal cord injuries achieves the intended effect if it is done within 8 hours of their onset; on the other hand, it has been pointed out that in cases where steroids were administered after 8 hours of the onsent, the amelioration of the neurological symptoms was less than achievable in a spontaneous course of time.

In any event, the conventional therapeutic regimen using steroids has substantial difficulties associated with the side effects of massive administration and is not a very convenient practical approach. Therefore, it is desired to develop a drug that causes less side effects than the existing drugs and that yet is effective in the treatment of various spinal cord injuries.

DISCLOSURE OF INVENTION

The present inventors conducted intensive studies with a view to attaining the stated object and unexpectedly found that nicaraven was what sought for and proved to be highly effective against spinal cord injuries. The present invention has been accomplished on the basis of this finding.

Nicaraven is a compound known to be useful as a thrombolytic agent, an anti-arteriosclerotic agent, a vasospasm inhibitor, an organ preservative, a radiation damage inhibitor, and so forth (see Japanese Patent Public Disclosure Nos. 75474/1981, 279328/1991, 145057/1994, 17801/1995, etc.); however, its effectiveness against spinal cord injuries has not been known at all.

BRIEF DESCRIPTION OF DRAWINGS

In FIG. 1, (■) represents the group administered physiological saline, ✱ a group administered nicaraven (1.0 mg/kg/min), ◨ another group administered nicaraven (0.1 mg/kg/min), ◩ the group subjected to the combination of nicaraven administration (1.0 mg/kg/min) and hypothermal spinal therapy, (*) p<0.05 vs baseline (ANOVA), and (#) p<0.05 vs the group administered physiological saline (ANOVA).

In FIG. 2 (■) represents the group administered physiological saline, ✱ a group administered nicaraven (1.0 mg/kg/min), ◨ another group administered nivaraven (0.1 mg/kg/min), ◩ the group subjected to the combination of nicaraven administration (1.0 mg/kg/min) and hypothermal spinal therapy, (*) p<0.05 vs baseline (ANOVA), and (#) p<0.05 vs the group administered physiological saline (ANOVA).

FIG. 3 shows the pathological changes that occurred in slices of the spinal cord 4 hours after its injury. In FIGS. 3A and 3B, the shaded areas represent the necrotic cell region; in FIGS. 3C and 3D, the dotted areas represent the neurons having a silver deposit. FIGS. 3A and 3C show the results with the untreated group (n=5), whereas FIGS. 3B and 3D show the results with the nicraven-treated group (n=5). In FIGS. 3A and 3B, the shaded (■) areas represent the necrotic cell region and in FIGS. 3C and 3D, the dotted ▨ areas represent the neurons having a silver deposit.

BEST MODE FOR CARRYING OUT THE INVENTION

Figure 1:
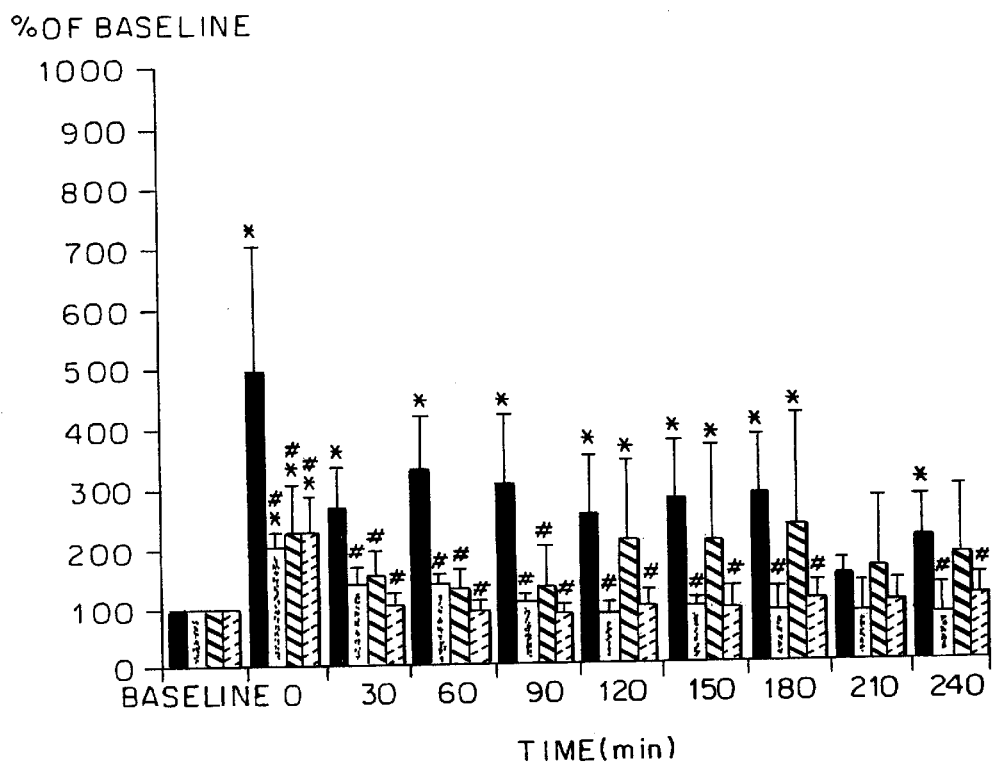
FIG. 1 is a graph showing the time profiles of glutamate release into spinal fluid after spinal cord injury. The values at respective times were determined as follows: two dialyses were done, each for a period of 10 minutes from 30 minutes before injury, the dialyzates were taken and their average glutamate concentration was determined as 100 (baseline); similarly, dialysis was done for a period of 10 minutes from the time of injury (0 min), 30, 60, 90, 120, 150, 180, 210 and 240 minutes after the injury, the dyalyzates were taken and their glutamate concentrations were determined as relative values expressed as percentage of the baseline.

The (±)-N,N'-propylene dinicotinamide (commonly known as "nicaraven") which is the efficaceous ingredient in the present invention is a known compound and may be prepared by the methods described in Japanese Patent Public Disclosure Nos. 75474/1981, 256664/1990, etc.

Nicaraven which is the efficaceous ingredient to be used in the present invention may form acid addition salts with pharmaceutically acceptable organic or inorganic acids and such salts can also be used in the invention. Examples of such acid addition salts include hydrochlorides, hydrobromates, sulfates, phosphates, nitrates, oxalates, lactates, tartrates, acetates, salicylates, benzoates, formates, propionates, pivalates, diethylacetates, malonates, succinates, pimelates, fumarates, maleates, malates, sulfamates, phenylpropionates, gluconates, ascorbates, isonicotinates, mathanesulfonates, p-toluenesulfonates, citrates, adipates, naphthalenedisulfonates, and so forth.

The therapeutic agent of the invention for treating spinal cord injuries has the advantage of healing or ameliorating spinal cord injuries, preventing the transition from an incomplete cord injury to a complete injury, and minimizing the consequences of spinal cord injuries including neurological disorders such as quadriplegia, paralysis of the respiratory muscle, damage to sensory functions and impairment of reflex functions, as well as impaired urinating or defecating functions.

The therapeutic agent of the invention for treating spinal cord injuries may be administered to the human body, either orally or parenterally such as by intrarectal, subcutaneous, intramedullary, intramuscular, intravenous, intraarterial and percutaneous routes; intravenous or intramedullary administration is preferred. For administration to the human body, nicaraven or its salts are preferably formulated in suitable dosage forms, such as tablets, powders, granules, subtilized granules, pills, capsules, lozenges, chewables, solutions, emulsions, suspensions, suppositories, syrups, lotions, ointments, cataplasms and so forth. These dosage forms can be formulated using pharmaceutically acceptable vehicles, excipients and other suitable additives.

A liquid is the dosage form that is preferred for intravenous or intramedullary administration of the therapeutic agent of the invention for treating spinal cord injuries. For preparing liquids, solvents can be used, as exemplified by purified water, physiological saline, alcohols such as ethanol, propylene glycol, glycerin and polyethylene glycol, and triacetin. The thus prepared liquids may be used as dilutions with a lactated Ringer's solution, a maintaining solution, a postoperative recovery fluid, a solution for supplying water to compensate for dehydration, physiological saline for use in dripping. The preparations may further be admixed with adjuvants such as antiseptics, moistening agents, emulsifiers, dispersing agents and stabilizers. Suspensions are another preferred dosage form to be administered.

Solid preparations such as tablets, pills, powders, granules, subtilized granules, lozenges and chewables may be formulated by common techniques in the presence of suitable vehicles such as sodium hydrogencarbonate, calcium carbonate, starch, sucrose, mannitol and carboxymethylcellulose, and other additives including calcium stearate, magnesium stearate and glycerin. Enteric preparations may also be formulated by applying an enteric coat from the spray of solution in organic solvents or water of enteric substances such as cellulose acetate phthalate, hydroxypropylmethylcellulose phathalate, polyvinyl alcohol phthalate, styrene-maleic acid copolymer and methacrylic acid-methyl methacrylate copolymer. Other common pharmaceutically acceptable vehicles include adjuvants, fragrances, stabilizers and antiseptics that may be used as required.

The therapeutic agent of the invention for treating spinal cord injuries may also be used in combination or admixture with other medications including steroids such as methylprednisolone and dexamethasone or other curatives of neurological disorders. The agent may even be used at different times of administration than said other medications.

If desired, the therapeutic agent of the invention for treating spinal cord injuries may be used in combination with hypothermal spinal therapy that has a cell protecting action.

In the invention, nicaraven or its salts may be administered in doses that are appropriately determined by the condition of the patient to be treated, his or her physique, age and sex, as well as the route of administration and dosage form. Generally, they are used in such amounts that their concentration in blood or spinal fluid ranges from $10^{-8}$ to $10^{-2}$ mol/mL, preferably from $10^{-5}$ to $10^{-3}$ mol/mL

EXAMPLES

The following examples are provided for further illustrating the present invention but are in no way to be taken as limiting.

Example 1

SD rats weighing 300–350 g were preliminarily subjected to surgical operations for removing the vertebral column at the lumbar level under anesthetization with halothane (2% through mask) and embedding of a loop-type microdialysis catheter (hollow fibers of a Cuprophan membrane, 18 cm long; i.d., 200 μm; cutoff, 45 kDa) with the subarachnoid space from the basal cisterns according to the method of Marsala et al. (J. Neurosci. Method, 63, 43–53, 1995). The catheter was retained such that its tip was positioned at the level of the interspace between lumbar segments 11 and 12. All animals that developed postoperative neurological disorders or symptoms of stress were excluded from the experiment and killed with a drug.

Figure 2:
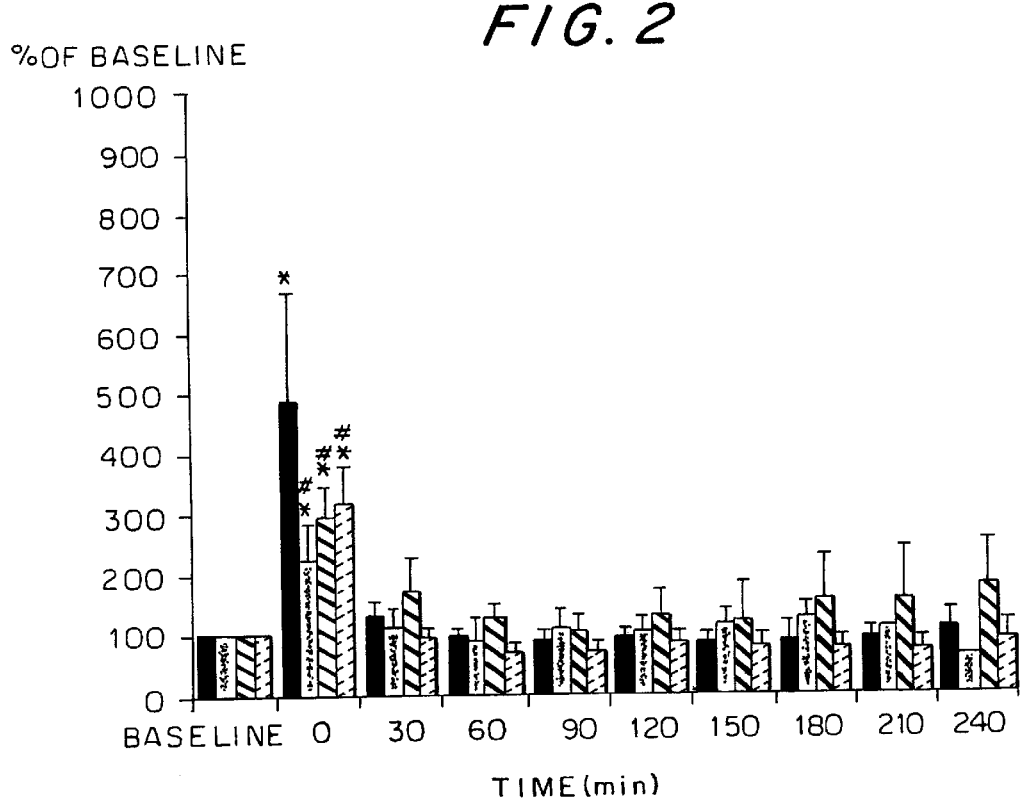
FIG. 2 is a graph showing the time profiles of taurine release into spinal fluid after spinal cord injury. The values at respective times were determined as follows; two dialyses were done, each for a period of 10 minutes from 30 minutes before injury, the dialyzates were taken and their average taurine concentration was determined as 100 (baseline); similarly, dialysis was done for a period of 10 minutes from the time of injury (0 min), 30, 60, 120, 150, 180, 210 and 240 minutes after the injury, the dyalyzates were taken and their glutamate concentrations were determined as relative values expressed as percentage of the baseline.
Figure 3C:
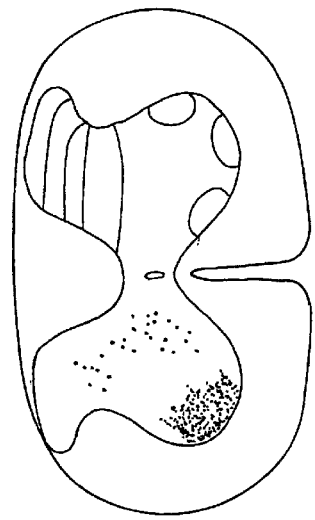
FIGS. 3C and 3D visualize the pathological findings at the level of the LIII-IV interspace (LIII stands for lumbar segment 3 and IV lumbar segment 4). The level of the LI-II interspace is the site where the spinal cord was directly compressed and the level of the LIII-IV interspace is the site around the compressed spinal cord. Each of the slices in FIG. 3 represents the accumulation of necrotic cells and neurons having a silver deposit (the cells that underwent the degeneration of axons and cytoplasm) in groups of animals each consisting of five.
Figure 3D:
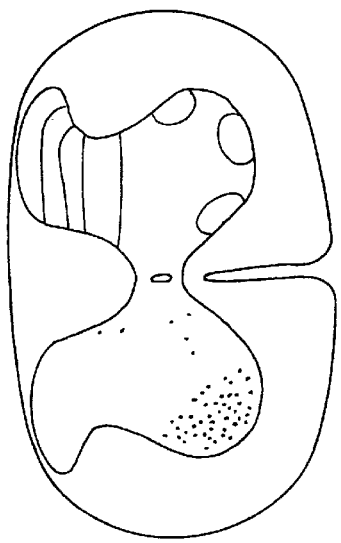
Figure 3A:
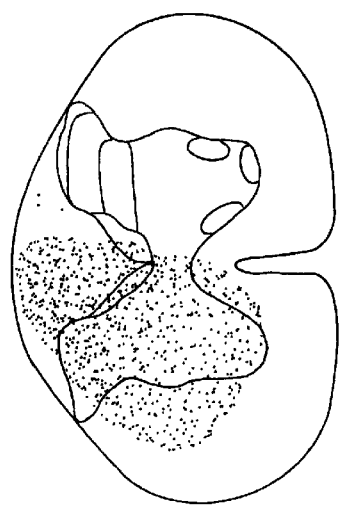
FIGS. 3A and 3B visualize the pathological findings at the level of the LI-II interspsce (LI stands for lumbar segment 1 and II lumbar segment 2) in an untreated group and a nicaraven-treated group, respectively.
Figure 3B:
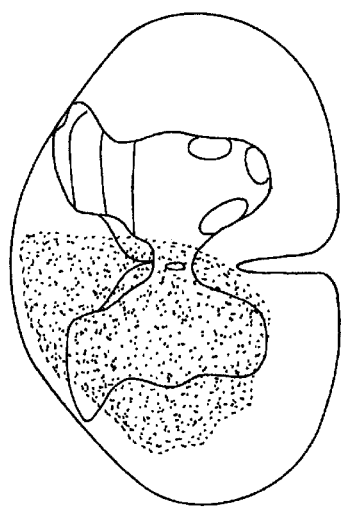

Three days later, the rats were divided into four groups, an untreated group (injected with physiological saline constantly to give the same volume as the drug solution), two nicaraven administered groups (0.1 and 1.0 mg/kg/min, i.v., 10 min), and a group subjected to the combination of nicaraven administration (1.0 mg/kg/min, i.v., 10 min) and hypothermal spinal therapy (33° C., contact with an ice bag). The surgical site in the lumbar segments was reopened under anesthetization with halothane (1% through mask) and after a rest for at least 30 minutes, a reference dialyzate (baseline) was taken. To establish a spinal, cord injury, a 2F-Fogarty balloon catheter was retained in the lower peridural space of the lumbar segments under a surgical microscope (Zeiss)

and filled with 0.1 mL of physiological saline. After 1-min compression, the peridural space was opened, the dialyzate was taken for as long as four hours and the concentrations of glutamate (Glu) and taurine (Tau) were measured by an OPA derivatization method (HPLC-ECD of Eicom Co.). Three other random groups of rats, 1) a pseudo-operation group, 2) an untreated group and 3) a nicaraven-treated group (1.0 mg/kg/min, i.v., 10 min), were not subjected to a microdialysis method but received the treatment described above and checked for any pathological changes in the spinal cord. Four hours after removal of the compression, the spinal cord was perfused with physiological saline and fixed with 4% neutral formalin, each being administered through the left ventricle, under inhalation of halothane (2%)/oxygen. The spinal cord tissue in the thoracic to the lumbar segments was extracted and immersed in 10% formaline for 7 days. Subsequently, the extracted tissue was dehydrated with saccharose (5–20%) for 24 hours and then frozen. Slices of the frozen tissue (20 μm thick) were prepared at −20° C. or below and stained by Nauta's method; thereafter, the number of cells with degenerating axons and cytoplasma (as evidenced by silver deposition) was counted with an optical microscope (×400) in tissue specimens from the level of the LI-II interspace corresponding to the site of direct injury and those from the level of the nearby LIII-IV interspace. The results of the experiments are shown in FIGS. 1, 2 and 3. FIGS. 3A and 3B represent the pathological findings from the untreated and nicaraven-treated groups at the level of the LI-II interspace (LI stands for lumbar segment 1 and II lumbar segment 2), whereas FIGS. 3C and 3D represent the pathological findings from the untreated and nicaraven-treated groups at the level of the LIII-IV interspace (LIII stands for lumbar segment 3 and IV lumbar segment 4). Each of the slices in FIG. 3 represents the accumulation of necrotic cells and neurons having a silver deposit (the cells that underwent the degeneration of axons and cytoplasm) in groups of animals each consisting of five. In FIGS. 3A and 3B, the shaded areas represent the necrotic cell region; in FIGS. 3C and 3D, the dotted areas represent the neurons having a silver deposit.

A marked increase in the concentrations of amino acids such as Glu and Tau after a spinal cord injury is considered to be one of the most important mechanisms involved as a secondary traumatic factor after the spinal cord injury. From the results of the experiments described above, it was found that in the pseudo-operation group, there was no change in the concentrations of amino acids during the four hours of measurement but that in the untreated group, Glu and Tau increased markedly by 6- and 4-folds, respectively, right after the spinal cord injury, with the Glu level remaining 2 to 3 times as high even after 4 hours. Thus, it was revealed that the sustained intravenous administration of nicaraven could suppress the increase in those amino acids in a dose-dependent manner (0.1–1.0 mg/kg/min). The group subjected to the combination of nicaraven administration and hypothermal spinal therapy showed substantially the same result as the group solely administered with nicaraven. Pathologically, there was no difference between the untreated group and the nicaraven-treated group at the level of the LI-II interspace which was subjected to direct spinal cord compression and hemorrhage and necrosis were found to have occurred over a wide range. However, at the level of the LIII-IV interface, silver deposition was positive in part of the internuncial neurons in the third to the fourth layer and in almost all motor neurons in the eighth to the ninth layer in the untreated group. In terms of the number of cells having a silver deposit, no positive cells (0±0) were found in the pseudo-operation group but in the untreated group, the number of positive cells was 19±1.6; in contrast, a lower number of positive cells (12±1.8) was established by the nicaraven-treated group. From these findings, one may well expect that nicaraven is effective against traumatic spinal cord injuries.

INDUSTRIAL APPLICABILITY

Nicaraven and its salts which are useful in the therapeutic agent of the invention for treating spinal cord injuries have less side effects than the conventional pharmacotherapeutic regimens and can heal or ameliorate spinal cord injuries, prevent the transition from an incomplete cord injury to a complete injury, and minimize the consequences of spinal cord injuries including neurological disorders such as quadriplegia, paralysis of the respitory muscle, damage to sensory functions and impairment of reflex functions, as well as impaired urinating or defecating function.

What is claimed is:

1. A method for treating or ameliorating neurological disorders that accompany spinal cord injuries comprising administering to a patient in need thereof an effective amount of (±)-N,N'-propylene dinicotinamide or a pharmaceutically acceptable salt thereof.

2. A method for treating spinal cord injuries comprising administering to a patient in need thereof an effective amount of (+)-N,N'-propylene dinicotinamide or a pharmaceutically acceptable salt thereof.

3. A method for treating spinal cord injuries in accordance with claim 2 wherein said administration is by injection.

4. A method for treating spinal cord injuries in accordance with claim 2, wherein said effective amount is such an amount as to provide a blood or spinal fluid concentration in the patient of $10^{-8}$ to $10^{-2}$ mol/mL.

5. A method for treating spinal cord injuries in accordance with claim 2, wherein said effective amount is such an amount as to provide a blood or spinal fluid concentration in the patient of $10^{-5}$ to $10^{-3}$ mol/mL.

6. A pharmaceutical agent composition in unit dosage form for spinal cord injuries which comprises (+)-N,N'-propylene dinicotinamide or a pharmaceutically acceptable salt thereof as an active ingredient in an amount sufficient upon administration to provide a blood or spinal fluid concentration of $10^{-8}$ mol/mL to $10^{-2}$ mol/mL;

a steroid effective for the amelioration of neurological symptoms associated with spinal cord injuries; and a pharmaceutically acceptable carrier or diluent.

7. The pharmaceutical agent composition of claim 6 wherein said steroid is methylprednisolone or dexamethasone.

8. A pharmaceutical agent composition in unit dosage form for treating or ameliorating neurological disorders that accompany spinal cord injuries, which comprises (+)-N,N'-propylene dinicotinamide or a pharmaceutically acceptable salt thereof as an active ingredient in an amount sufficient upon administration to provide a blood or spinal fluid concentration of $10^{-5}$ mol/mL to $10^{-3}$ mol/mL;

a steroid effective for the amelioration of neurological symptoms associated with spinal cord injuries; and a pharmaceutically acceptable carrier or diluent.

9. The pharmaceutical agent composition of claim 8 wherein said steroid is methylprednisolone or dexamethasone.

* * * * *

UNITED STATES PATENT AND TRADEMARK OFFICE
CERTIFICATE OF CORRECTION

PATENT NO. : 6,090,823
DATED : July 18, 2000
INVENTOR(S) : Toshio Ishikawa

It is certified that error appears in the above-identified patent and that said Letters Patent is hereby corrected as shown below:

Cover page, title line [54], delete

"REMEDY FOR SPINAL INJURY" and insert therefor

-- THERAPEUTIC AGENT FOR SPINAL CORD INJURIES --.

Signed and Sealed this

Twenty-second Day of May, 2001

Attest:

NICHOLAS P. GODICI

Attesting Officer     Acting Director of the United States Patent and Trademark Office